United States Patent
Tada

(10) Patent No.: US 8,591,108 B2
(45) Date of Patent: Nov. 26, 2013

(54) RADIATION IMAGING SYSTEM AND APPARATUS AND METHOD FOR DETECTING DEFECTIVE PIXEL

(75) Inventor: Takuji Tada, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 352 days.

(21) Appl. No.: 13/016,759

(22) Filed: Jan. 28, 2011

(65) Prior Publication Data

US 2011/0235775 A1     Sep. 29, 2011

(30) Foreign Application Priority Data

Mar. 26, 2010   (JP) ................................. 2010-072067
Sep. 22, 2010   (JP) ................................. 2010-211941

(51) Int. Cl.
*G01D 18/00*     (2006.01)
(52) U.S. Cl.
USPC ........................................... 378/207; 378/62
(58) Field of Classification Search
USPC ....................................... 378/36, 62, 82, 207
See application file for complete search history.

(56) References Cited

U.S. PATENT DOCUMENTS

| 7,746,981 | B2 | 6/2010 | Takahashi et al. | |
|---|---|---|---|---|
| 2011/0235779 | A1* | 9/2011 | Ishii ................................. | 378/62 |
| 2011/0243302 | A1* | 10/2011 | Murakoshi ........................ | 378/62 |
| 2012/0155610 | A1* | 6/2012 | Murakoshi et al. ............... | 378/62 |
| 2013/0010926 | A1* | 1/2013 | Tada ................................. | 378/62 |
| 2013/0083893 | A1* | 4/2013 | Ishii ................................. | 378/62 |

FOREIGN PATENT DOCUMENTS

| JP | 2002-197450 A | 7/2002 |
|---|---|---|
| JP | 2008-79923 A | 4/2008 |
| JP | 2008-200359 A | 9/2008 |
| JP | 2009-133823 A | 6/2009 |
| WO | WO 2008/102654 A1 | 8/2008 |
| WO | WO 2008/102685 A1 | 8/2008 |

OTHER PUBLICATIONS

"Differential x-ray phase contrast imaging using a shearing interferometer" (C. David, et al., Applied Physics Letters, vol. 81, No. 17, Oct. 2002, pp. 3287-3289).
"Improved phase-shifting method for automatic processing of moiré deflectograms" (Hector Canabal, et al., Applied Optics, vol. 37, No. 26, Sep. 1998, pp. 6227-6233).
Notification of Reasons for Refusal (Japan), dated Jul. 24, 2013, with English translation.

* cited by examiner

*Primary Examiner* — Glen Kao
(74) *Attorney, Agent, or Firm* — McGinn IP Law Group, PLLC

(57) ABSTRACT

An X-ray imaging system includes an X-ray source, first and second absorption gratings, and an FPD. The first absorption grating passes X-ray emitted from the X-ray source to form a G1 image. The second absorption grating modulates intensity of the G1 image at each of relative positions to form two or more fringe images. The relative positions differ in phase with respect to a period pattern of the G1 image. The FPD detects two or more frames of image data of the fringe images. A defective pixel detector reads two or more frames of image data stored in a memory and obtains a characteristic value of an intensity modulated signal on a pixel-by-pixel basis based on the read image data. The defective pixel detector detects a defective pixel based on the characteristic value obtained.

16 Claims, 12 Drawing Sheets

UNEVEN THICKNESS

IRREGULAR PITCH AND IRREGULAR OPENING SIZE

INCLINED

RADIATION IMAGING SYSTEM AND APPARATUS AND METHOD FOR DETECTING DEFECTIVE PIXEL

FIELD OF THE INVENTION

The present invention relates to a radiation imaging system for capturing an image of an object using radiation such as X-ray and more particularly to a radiation imaging system for performing radiation phase imaging using a grating arranged between a radiation source and a radiation image detector, and an apparatus and method for detecting a defective pixel of the radiation image detector.

BACKGROUND OF THE INVENTION

X-ray attenuates while it passes through a substance. The attenuation depends on an atomic number of an element constituting the substance and density and thickness of the substance. A probe for examining the inside of an object using X-ray exploits this X-ray attenuation property. X-ray imaging is commonly used in medical diagnoses and non-destructive inspections.

A common X-ray imaging system captures a radiograph or X-ray transmission image of an object arranged between an X-ray source for applying X-ray and an X-ray image detector for detecting the X-ray. The X-ray emitted from the X-ray source attenuates or is absorbed by the object depending on the object's properties (atomic number, density, thickness) while the X-ray passes through the object, and then enters each pixel in the X-ray image detector. Thereby, the X-ray image detector detects and produces an X-ray absorption image of the object. A flat panel detector (FPD), photostimulable phosphor, and a combination of an intensifying screen and a film are commonly used as the X-ray image detectors.

The X-ray absorption property of a substance decreases as the atomic number of the element constituting the substance decreases. This causes a problem that a sufficient contrast cannot be obtained in the X-ray absorption image of living soft tissue or soft materials. For example, cartilage in a joint of a human body and synovial fluid surrounding the cartilage are mainly made of water, so there is little difference between their amounts of X-ray absorption, resulting in little difference in contrast.

Recently, X-ray phase imaging has been studied actively to solve the above problem. The X-ray phase imaging obtains an image (hereafter referred to as phase contrast image) based on phase changes (angle changes), instead of intensity changes, of the X-ray caused by the object through which the X-ray passes. Generally, when the X-ray is incident on the object, the object interacts with the phase of the X-ray more strongly than with the intensity of the X-ray. Accordingly, the X-ray phase imaging using the phase difference obtains a high contrast image even if the object is composed of components with little difference in their X-ray absorptivity. Recently, an X-ray imaging system using an X-ray Talbot interferometer is devised as an example of the X-ray phase imaging. The X-ray Talbot interferometer is composed of an X-ray source, two transmission diffraction gratings, and an X-ray image detector (see, for example, Japanese Patent Laid-Open Publication No. 2008-200359, and C. David, et al., "Differential X-ray Phase contrast imaging using a shearing interferometer", Applied Physics Letters, Vol. 81, No. 17, October 2002, page 3287).

In an X-ray Talbot interferometer, an object is arranged between an X-ray source and a first diffraction grating. A second diffraction grating is arranged downstream of the first diffraction grating by the Talbot length defined by the grating pitch of the first diffraction grating and the X-ray wavelength. The X-ray image detector is arranged behind the second diffraction grating. A Talbot length is a distance between the first diffraction grating and a position at which the X-ray passed through the first diffraction grating forms a self image of the first diffraction grating due to the Talbot effect. The self image is modulated due to the interaction between the X-ray and the object arranged between the X-ray source and the first diffraction grating, namely, the interaction changes the phase of the X-ray.

The X-ray Talbot interferometer detects moiré fringes generated by superposition (intensity modulation) of the self image of the first diffraction grating and the second diffraction grating using a fringe-scanning method. Then the X-ray Talbot interferometer obtains a phase contrast image of the object H from changes in the moiré fringes caused by the object H. In the fringe-scanning method, images are captured while the second diffraction grating is translationally moved in a direction substantially parallel to the plane of the first diffraction grating and substantially vertical to the grating direction of the first diffraction grating at a scanning pitch which is one of equally-divided parts of a grating pitch, and then a phase differential image is obtained from a phase shift value of the intensity changes in the pixel data, obtained by each pixel in the X-ray image detector, caused by the scanning. The phase shift value is a value of the phase shift between the case where the object H is present and the case where the object H is absent. The phase differential image corresponds to angular distribution of the X-ray refracted by the object. The phase differential image is integrated in the fringe-scanning direction. Thereby, a phase contrast image of the object is obtained. Because the pixel data is a signal whose intensity is periodically modulated by the scanning, a set of pixel data obtained by the scanning is referred to as an intensity modulated signal. An imaging apparatus using laser light instead of X-ray also employs the fringe-scanning method (for example, see Hector Canabal, et al., "Improved phase-shifting method for automatic processing of moiré deflectograms" Applied Optics, Vol. 37, No. 26, September 1998, page 6227).

The X-ray imaging system employing the X-ray Talbot interferometer uses a solid-state imaging device, for example, the above-described FPD, which obtains pixel data as digital data, as the X-ray image detector. Such X-ray image detector is provided with a plurality of pixels. Inevitably, defective pixels occur. Here, the term "defective pixel" includes a physically defective pixel caused by production and the like and a pixel outputting an abnormal or unexpected signal value due to various reasons such as a flaw on a detection surface or a deposit of foreign matter although the pixel functions normally.

To correct the defective pixels, a technique to obtain positional information of the defective pixels in advance to perform correction processing to an X-ray imaging obtained by an X-ray image detector is known (see, for example, Japanese Patent Laid-Open Publication No. 2008-079923 and Japanese Patent Laid-Open Publication No. 2002-197450).

In the above-described X-ray imaging system, the first and second diffraction gratings are required to be produced with high precision and a small production error. Even a slight deformation in one of the first and second diffraction gratings causes a pixel in a position corresponding to the deformation to fail to detect a normal phase shift value. Such pixel functions as a defective pixel. A method for detecting defective pixels caused by the grating deformation has not been known.

Specific examples of the deformation of the first and second diffraction gratings include an irregular grating pitch, an irregular opening width, thickness unevenness of the grating, local inclination of the grating, and the like. Such deformation affects not only the X-ray transmittance but also the intensity modulated signal obtained with the positions of the first and second diffraction gratings relatively shifted. As a result, the detection accuracy of the phase shift value is degraded, making it difficult to detect defective pixels caused by the grating deformation based on the absorption image. This absorption image is obtained by X-ray imaging using the first and second diffraction gratings. The above-described Japanese Patent Laid-Open Publication No. 2008-079923 and Japanese Patent Laid-Open Publication No. 2002-197450 are not related to the X-ray phase imaging and do not touch upon the method for detecting the defective pixel caused by the grating deformation.

To obtain a phase contrast image from a phase differential image, the above-described X-ray imaging system requires an integration process in the fringe-scanning direction. One defective pixel results in linear artifact in the fringe-scanning direction, so it is desired to detect the defective pixel with high accuracy.

SUMMARY OF THE INVENTION

An object of the present invention is to provide a radiation imaging system and an apparatus and method for detecting with high accuracy a defective pixel caused by grating deformation.

In order to achieve the above and other objects, a defective pixel detection apparatus of the present invention used in a radiation imaging system includes a characteristic value obtaining section and a defective pixel detecting section. The radiation imaging system obtains a characteristic value from an intensity modulated signal on a pixel-by-pixel basis. The intensity modulated signal represents a relation between the relative position and a pixel value. The defective pixel detecting section detects a defective pixel based on the characteristic value. The radiation imaging system has a grating, an intensity modulator, and a radiation image detector. The grating passes radiation emitted from a radiation source to form a first fringe image. The intensity modulator modulates intensity of the first fringe image at each of relative positions to form two or more second fringe images. The relative positions differ in phase with respect to a period pattern of the first fringe image. The radiation image detector detects the second fringe image.

It is preferable that the characteristic value is at least one of an amplitude value, an average value, a maximum value, a minimum value, a variance, a standard deviation, visibility, and a period.

It is preferable that the characteristic value is the average value and the amplitude value, and the defective pixel detecting section detects the defective pixel based on a criterion dependent on the characteristic value.

It is preferable that the defective pixel detecting section further detects the defective pixel based on a dark image obtained by the radiation image detector in the absence of the radiation.

A defective pixel detection method used in a radiation imaging system includes an obtaining step and a detecting step. In the obtaining step, a characteristic value is obtained from an intensity modulated signal on a pixel-by-pixel basis. The intensity modulated signal represents a relation between the relative position and a pixel value. In the detecting step, a defective pixel is detected based on the characteristic value.

A radiation imaging system includes a grating, an intensity modulator, a radiation image detector, a characteristic value obtaining section, a defective pixel detecting section. The grating passes radiation emitted from a radiation source to form a first fringe image. The intensity modulator modulates intensity of the first fringe image at each of relative positions to form two or more second fringe images. The relative positions differ in phase with respect to a period pattern of the first fringe image. The radiation image detector detects the second fringe images. The characteristic value obtaining section obtains a characteristic value from an intensity modulated signal on a pixel-by-pixel basis. The intensity modulated signal represents a relation between the relative position and a pixel value. The defective pixel detecting section detects a defective pixel based on the characteristic value.

It is preferable that the characteristic value is at least one of an amplitude value, an average value, a maximum value, a minimum value, a variance, a standard deviation, visibility, and a period.

It is preferable that the characteristic value is the average value and the amplitude value, and the defective pixel detecting section detects the defective pixel based on a criterion dependent on the characteristic value.

It is preferable that the radiation imaging system further includes storage for storing position information of the defective pixel detected by the defective pixel detecting section.

It is preferable that the position information stored in the storage is updated when new position information of the defective pixel is generated by the defective pixel detecting section.

It is preferable that the defective pixel detecting section further detects the defective pixel based on a dark image obtained by the radiation image detector in the absence of the radiation.

It is preferable that the defective pixel detecting section stores the position information of the defective pixel detected based on the dark image separately from the position information of the defective pixel detected based on the characteristic value of the intensity modulated signals in a distinguishable manner in the storage.

It is preferable that the intensity modulator is composed of a second grating having a periodic pattern in the same direction as the first fringe image, and a scanning section for moving at least one of the first grating and the second grating at a predetermined pitch.

It is preferable that the first and second gratings are absorption gratings.

It is preferable that the first grating is a phase grating.

It is preferable that each of the pixel has a conversion layer for converting the radiation into electric charge and a charge collection electrode for collecting the electric charge. The charge collection electrode is composed of multiple linear electrode groups arranged to have mutually different phases. The linear electrode groups have periodic patterns in the same direction as the second fringe images. The intensity modulator is composed of the charge collection electrode.

According to the defective pixel detection apparatus and the defective pixel detection method of present invention, the defective pixel is detected using the characteristic value of the intensity modulated signal from each pixel based on the fringe images obtained by the radiation image detector when the radiation is emitted from the radiation source. Thereby, the defective pixel caused only by the grating is detected with accuracy. More specifically, the defective pixel is detected based on the average value and the amplitude value of the intensity modulated signal. Thereby, the defective pixel caused by the grating deformation is detected with high accuracy.

BRIEF DESCRIPTION OF THE DRAWINGS

The above and other objects and advantages of the present invention will be more apparent from the following detailed description of the preferred embodiments when read in connection with the accompanied drawings, wherein like reference numerals designate like or corresponding parts throughout the several views, and wherein.

DESCRIPTION OF THE PREFERRED EMBODIMENTS (First Embodiment)

Figure 1:
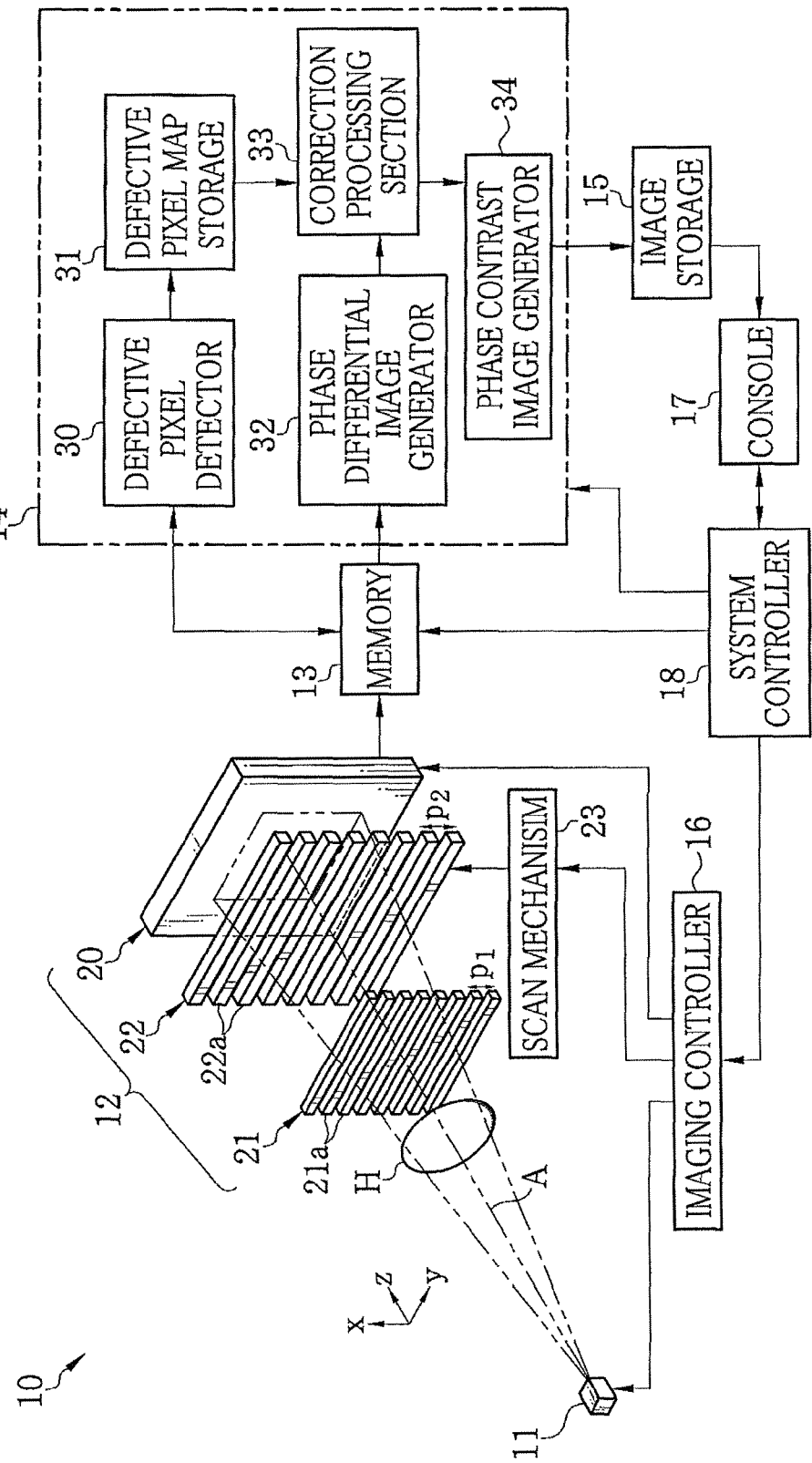
FIG. 1 is a diagram showing a configuration of an X-ray imaging system according to a first embodiment of the present invention.

In FIG. 1, an X-ray imaging system 10 according to a first embodiment of the present invention is composed of an X-ray source 11, an imaging unit 12, a memory 13, an image processor 14, an image storage 15, an imaging controller 16, a console 17, and a system controller 18. The X-ray source 11 applies X-ray to an object H. The imaging unit 12 is opposed to the X-ray source 11 and detects the X-ray, emitted from the X-ray source 11 and passed through the object H, to generate image data. The memory 13 stores the image data read from the imaging unit 12. The image processor 14 processes multiple frames of image data stored in the memory 13 to generate a phase contrast image. The image storage 15 stores the phase contrast image generated by the image processor 14. The imaging controller 16 controls the X-ray source 11 and the imaging unit 12. The console 17 is composed of an operating section, a monitor, and the like. The system controller 18 controls the overall operation of the X-ray imaging system 10 based on an operation signal inputted through the console 17.

The X-ray source 11 is composed of a high voltage generator, an X-ray tube, a collimator, and the like (all not shown). Under the control of the imaging controller 16, the X-ray source 11 irradiates the object with the X-ray. The X-ray tube is, for example, a rotating anode type X-ray tube. The X-ray tube emanates electron beams from a filament in accordance with voltage from the high voltage generator. The electron beams impinge on an anode rotating at a predetermined speed to generate the X-ray. The rotating anode prevents the electron beams from impinging on the same spot and thus reduces deterioration of the rotating anode. A spot of the rotating anode on which the electron beams impinge is an X-ray focal point. The X-ray is emitted from the X-ray focal point. The collimator restricts an X-ray irradiation field of the X-ray tube to shield an area of the object H other than the area under examination from the X-ray.

The imaging unit 12 is provided with a flat panel detector (hereafter referred to as FPD) 20, a first absorption grating 21, and a second absorption grating 22. The FPD 20 is composed of a semiconductor circuit. The first absorption grating 21 and the second absorption grating 22 are used for detecting phase changes (angle changes) of the X-ray caused by the object H to perform phase imaging. The FPD 20 is arranged such that its detection surface is orthogonal to a direction (hereafter, referred to as z direction) of an optical axis A of the X-ray emitted from the X-ray source 11.

The first absorption grating 21 has a plurality of X-ray shield members 21a. The X-ray shield members 21a extend in a direction (hereafter referred to as y direction) in a plane orthogonal to the z direction, and arranged at a predetermined pitch $p_1$ in a direction (hereafter referred to as x direction) orthogonal to the z direction and the y direction. Likewise, the second absorption grating 22 has a plurality of X-ray shield members 22a arranged at a predetermined pitch $p_2$ in the x direction. The X-ray shield members 22a extend in the y direction. It is preferable that the X-ray shield members 21a and 22a are made of metal having excellent X-ray absorption property, for example, gold, silver, or platinum.

The imaging unit 12 is provided with a scan mechanism 23. The scan mechanism 23 translationally moves the second absorption grating 22 in a direction (x direction) orthogonal to the grating direction to change the position of the second absorption grating 22 relative to the position of the first absorption grating 21. The scan mechanism 23 is composed of an actuator, for example, a piezoelectric element. To perform the fringe-scanning, which will be described later, the scan mechanism 23 is driven under the control of the imaging controller 16. Image data obtained by the imaging unit 12 in each scanning step or position of the fringe-scanning is stored in the memory 13. The second absorption grating 22 and the scan mechanism 23 constitute an intensity modulator.

The image processor 14 is provided with a defective pixel detector 30 and a defective pixel map storage 31. The defective pixel detector 30 detects a defective pixel of the FPD 20 from the image data obtained during the calibration to create a defective pixel map (positional information of one or more defective pixel). The defective pixel map created is stored in the defective pixel map storage 31. If the defective pixel map storage 31 already contains a defective pixel map, the existing defective pixel map is overwritten with the new defective pixel map created. Thus, the defective pixel map is updated.

The image processor 14 further includes a phase differential image generator 32, a correction processing section 33, and a phase contrast image generator 34. The phase differential image generator 32 generates or produces a phase differential image based on multiple frames of image data captured by the imaging unit 12 and stored in the memory 13 in each scanning step or position of the fringe-scanning. The correction processing section 33 performs defective pixel correction to the phase differential image based on the defective pixel map stored in the defective pixel map storage 31. The phase contrast image generator 34 integrates the corrected phase differential image in the x direction to produce the phase contrast image. The phase contrast image is stored in the image storage 15. Then, the phase contrast image is outputted to the console 17 and displayed on the monitor (not shown). Instead of the phase contrast image, the phase differential image may be stored in the image storage 15 and then displayed on the monitor.

The console 17 is provided with the monitor and the operating section (not shown). An operator inputs an instruction for imaging and details of the instruction using the operating section. Examples of the operating section include a switch, a touch panel, a mouse, and a keyboard. Operating the operating section, the operator inputs a tube voltage of the X-ray tube, an X-ray imaging condition such as X-ray irradiation time, imaging timing, and the like. The monitor is an LCD, CRT, or the like. The monitor displays text information such as the X-ray imaging condition and the phase contrast image.

Figure 2:
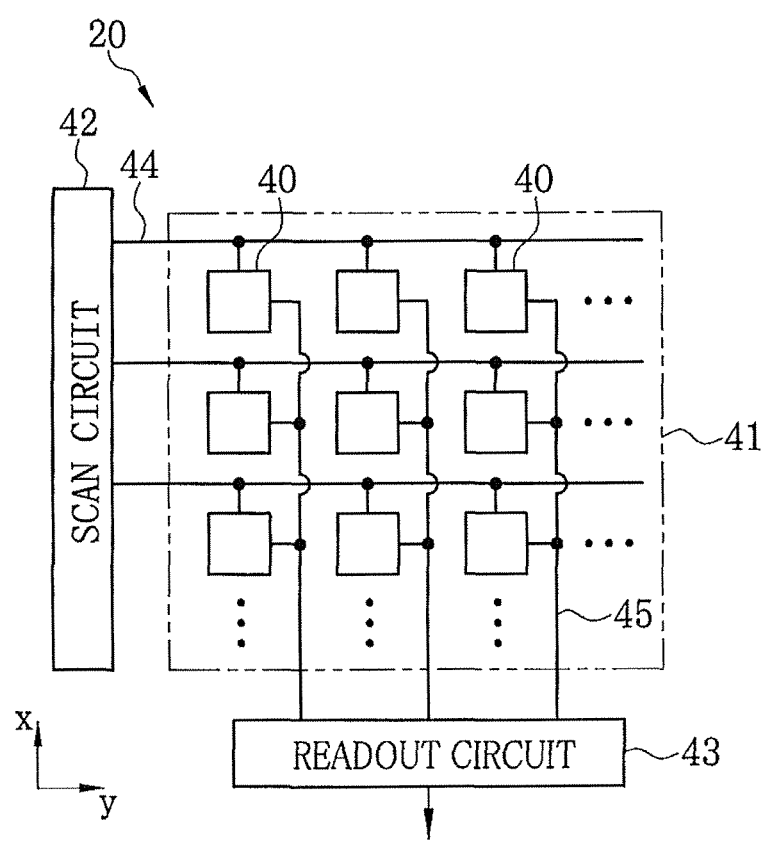
FIG. 2 is a diagram showing a configuration of a flat panel detector.

In FIG. 2, the FPD 20 is composed of an imaging section 41, a scan circuit 42, a readout circuit 43. The imaging section 41 is composed of pixels 40 arranged in two dimensions (x and y directions) on an active matrix substrate. Each pixel 40 converts the X-ray into electric charge and accumulates the electric charge. The scan circuit 42 controls timing to read the electric charge from the imaging section 41. The readout circuit 43 reads the electric charge accumulated in each pixel 40 to convert the electric charge into image data and stores the image data. A scan line 44 connects the scan circuit 42 and the pixels 40 in each row. A signal line 45 connects the readout circuit 43 and the pixels 40 in each column. The pixels 40 are arranged at a pitch of approximately 100 µm in the x and y directions.

The pixels 40 are direct conversion type X-ray sensing elements. In this case, each of the pixels 40 directly converts the X-ray into the electric charge using a conversion layer(not shown) made from amorphous selenium and the like and then accumulates the electric charge in a capacitor (not shown) connected to an electrode below the conversion layer. To each pixel 40, a TFT switch (not shown) is connected. A gate electrode of the TFT switch is connected to the scan line 44. A source electrode is connected to the capacitor. A drain electrode is connected to the signal line 45. When a drive pulse from the scan circuit 42 turns on the TFT switch, the electric charge accumulated in the capacitor is transferred to the signal line 45.

Alternatively, the pixels 40 may be indirect conversion type X-ray sensing elements. In this case, each of the pixels 40 converts the X-ray into visible light using a scintillator (not shown) made from gadolinium oxide ($Gd_2O_3$), cesium iodide (CsI), or the like and then converts the visible light into electric charge using a photodiode (not shown) to accumulate the electric charge. In this embodiment, the FPD having a TFT panel is used as the radiation image detector. Alternatively or in addition, various types of radiation image detectors having a solid image sensor such as a CCD sensor or a CMOS sensor may be used.

The readout circuit 43 is composed of an integrating amplifier, a correction circuit, an A/D converter, and the like (all not shown). The integrating amplifier integrates the electric charge outputted from each of the pixels 40 through the signal lines 45 to convert the electric charge into a voltage signal (image signal). The A/D converter converts the image signal into digital image data. The correction circuit performs offset correction, gain correction, linearity correction, and the like to the image data. The correction circuit inputs the corrected image data to the memory 13.

Figure 3:
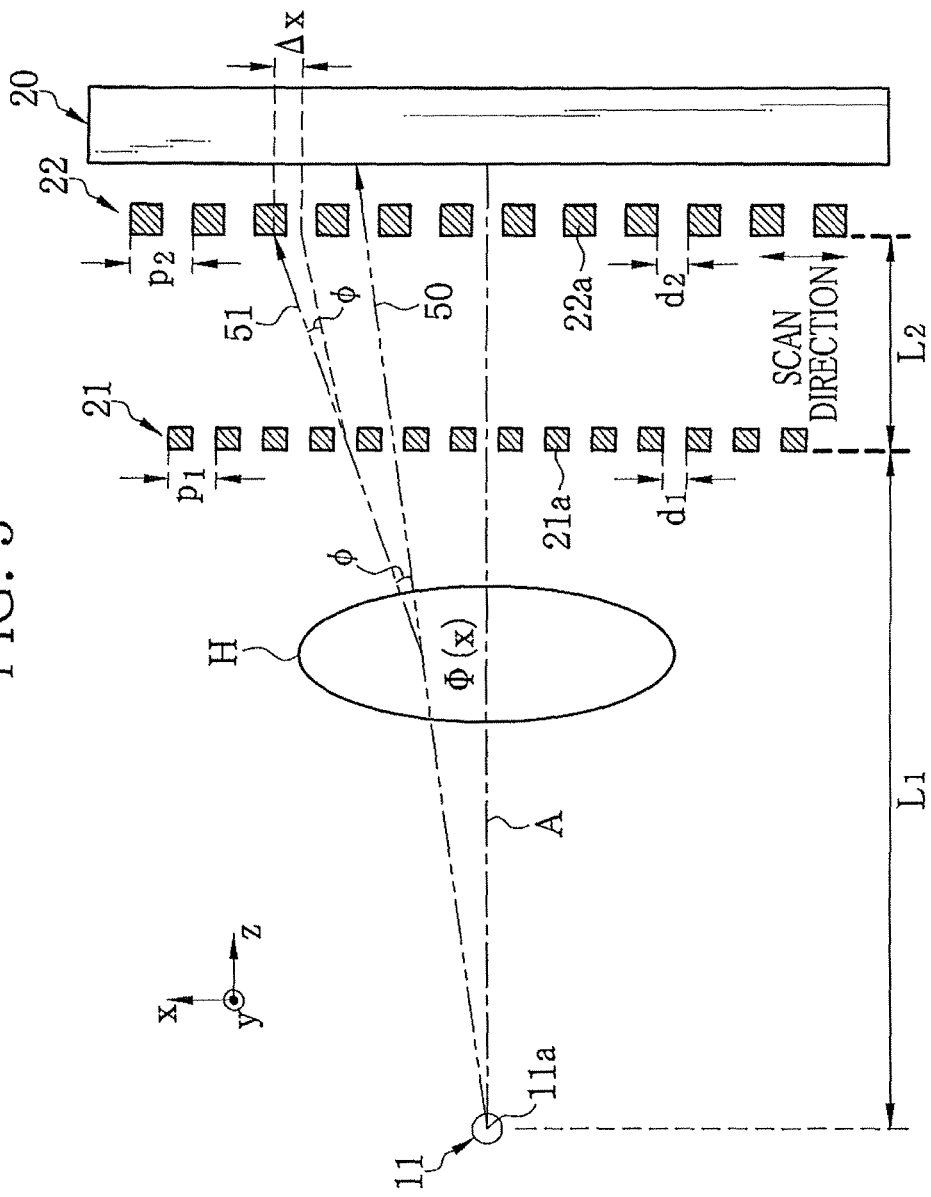
FIG. 3 is a schematic lateral view showing a configuration of first and second absorption gratings.

As shown in FIG. 3, the X-ray shield members 21a of the first absorption grating 21 are arranged at a predetermined pitch $p_1$ in the x direction with a predetermined spacing $d_1$. Similarly, the X-ray shield members 22a of the second absorption grating 22 are arranged at a predetermined pitch $p_2$ in the x direction with a predetermined spacing $d_2$. The X-ray shield members 21a and 22a are arranged on X-ray transmission substrates, for example, glass substrates, respectively (not shown). The first and second absorption gratings 21 and 22 are referred to as amplitude gratings, because the first and second absorption gratings 21 and 22 do not change the phase of the incident X-ray but change the intensity of the incident X-ray. Slits between the X-ray shield members 21a (areas with the spacing $d_1$) and the slits between the X-ray shield members 22a (areas with the spacing $d_2$) may not be gaps or empty spaces. The slits may be filled with a low X-ray absorption material, for example, polymer or light metal.

Regardless of the presence or absence of the Talbot effect, the first and second absorption gratings 21 and 22 are arranged to form a linear projection of the X-ray passing through the slits. To be more specific, each of the spacings $d_1$ and $d_2$ is set at the size sufficiently larger than a peak wavelength of the X-ray emitted from the X-ray source 11. Thereby, most of the emitted X-ray passes through the slits in straight lines without diffraction at the slits. For example, when the rotating anode 18a of the X-ray tube is made from tungsten and the tube voltage is 50 kV, the peak wavelength of the X-ray is approximately 0.4 Å. In this case, most of the X-ray is linearly projected without diffraction at the slits when each of the spacings $d_1$ and $d_2$ is at a value in a range approximately from 1 µm to 10 µm. Each of the grating pitches $p_1$ and $p_2$ is at a value in a range approximately from 2 µm to 20 µm.

The X-ray source 11 emits the X-ray not in parallel beams but in cone beams having an X-ray focal point 11a as a light emission point. Accordingly, a projection or projected image (hereafter referred to as G1 image or fringe image) of the first absorption grating 21 projected or formed by the X-ray passed through the first absorption grating 21 is enlarged in proportion to a distance from the X-ray focal point 11a. The grating pitch $p_2$ of the second absorption grating 22 is determined such that the slits of the second absorption grating 22 substantially coincide with the periodic pattern of the bright areas in the G1 image at the second absorption grating 22. When $L_1$ denotes a distance between the X-ray focal point 11a and the first absorption grating 21 and $L_2$ denotes a distance between the first absorption grating 21 and the second absorption grating 22, the grating pitch $p_2$ is determined to satisfy a mathematical expression (1).

$$p_2 = \frac{L_1 + L_2}{L_1} p_1 \qquad (1)$$

In the Talbot interferometer, the distance $L_2$ between the first absorption grating 21 and the second absorption grating 22 is restricted by the Talbot length that is defined by the grating pitch $p_1$ of the first diffraction grating 21 and the X-ray wavelength. In the imaging unit 12 of this embodiment, on the other hand, the first absorption grating 21 projects the incident X-ray without diffraction. An image similar to the G1 image of the first absorption grating 21 is obtained at any position behind the first absorption grating 21. As a result, the distance $L_2$ can be set independently of or without reference to the Talbot length.

As described above, the imaging unit 12 of this embodiment is not a Talbot interferometer. With the assumption that the X-ray is diffracted by the first absorption grating 21 to produce the Talbot effect, a Talbot length Z is represented by a mathematical expression (2) where $p_1$ denotes the grating pitch of the first absorption grating 21, $p_2$ denotes the grating pitch of the second absorption grating 22, λ denotes the X-ray wavelength (the peak wavelength), and m denotes a positive integer.

$$Z = m\frac{p_1 p_2}{\lambda} \qquad (2)$$

The mathematical expression (2) represents the Talbot length when the X-ray from the X-ray source 11 is a cone beam. The mathematical expression (2) is disclosed in "Sensitivity of X-ray phase Imaging based on Talbot Interferometry" (Atsushi Momose, et al., Japanese Journal of Applied Physics, Vol. 47, No. 10, October 2008, page 8077).

In this embodiment, the distance $L_2$ can be set independently of the Talbot length as described above. To make the imaging unit 12 slim or low-profile in the z direction, the distance $L_2$ is set to be shorter than the minimum Talbot length Z obtained when m=1. Namely, the distance $L_2$ is set at a value in a range satisfying a mathematical expression (3), $$L_2 < \frac{p_1 p_2}{\lambda} \qquad (3)$$

To generate a periodic pattern image with high contrast, it is preferable that the X-ray shield members 21a and 22a completely shield (absorb) the X-ray. Although the above-described materials (gold, silver, or platinum) having the high X-ray absorption property are used, the transmission X-ray, which has not been absorbed by the X-ray shield members 21a and 22a, exists to a certain extent. To improve the X-ray shield (absorption) property, it is preferable to increase, as much as possible, the thickness in the z direction of each of the X-ray shield members 21a and 22a, that is, an aspect ratio. For example, it is preferable to shield (absorb) at least 90% of the irradiation X-ray when the tube voltage of the X-ray tube is 50 kV. In this case, it is preferable that the thickness of each of the X-ray shield members 21a and 22a is at least 30 μm (Au equivalent thickness).

With the use of the first and second absorption gratings 21 and 22, the intensity of the fringe image is modulated by the superposition of the G1 image of the first absorption grating 21 and the second absorption grating 22. The FPD 20 captures an image of the modulated fringe image. There is a slight difference between a pattern period of the G1 image at the second absorption grating 22 and the grating pitch $p_2$ of the second absorption grating 22 due to production error and layout error. This slight difference causes moiré fringes in the intensity-modulated fringe image. So-called rotational moiré fringes occur when there is an error in the grating arrangement direction of the first and second absorption gratings 21 and 22, that is, the grating arrangement directions of the first and second absorption gratings 21 and 22 are different. Such moiré fringes do not raise a problem as long as the period of the moiré fringes in the x or y direction is larger than the arrangement pitch of the pixels 40. If possible, it is preferable to prevent the occurrence of moiré fringes. The moiré fringes, however, can be used for checking a scanning amount of the fringe-scanning, that is, a distance of the translational movement of the second absorption grating 22.

When the object H is arranged between the X-ray source 11 and the first absorption grating 21, the fringe image changed or modulated by the object H is detected by the FPD 20. An amount of the change or modulation is in proportion to an angle of the X-ray deflected by the refraction of the object H. Analyzing the fringe image detected by the FPD 20 produces the phase contrast image of the object H.

Next, an analytical method of the fringe image is described. FIG. 3 shows an X-ray path 50 where the object H is absent and an X-ray path 51 where the object H is present. When the object H is absent, the X-ray traveling along the X-ray path 50 passes through the first and second absorption gratings 21 and 22 and then enters the FPD 20. On the other hand, when the object H is present, the X-ray path 51 is refracted in accordance with the phase shift distribution Φ(x) in the x direction of the object H. In this case, the X-ray traveling along the X-ray path 51 passes through the first absorption grating 21, and then is shielded by the X-ray shield member 22a of the second absorption grating 22.

The phase shift distribution Φ(x) of the object H is represented by a mathematical expression (4) where "n(x, z)" denotes refractive index distribution of the object H, "z" denotes an X-ray traveling direction. Here, for the sake of simplicity, the y coordinate is omitted.

$$\Phi(x) = \frac{2\pi}{\lambda} \int [1 - n(x, z)] dz \qquad (4)$$

The G1 image projected from the first absorption grating 21 to the second absorption grating 22 is displaced in the x direction with an amount corresponding to a refraction angle φ of the X-ray refracted by the object H. Because the refraction angle φ of the X-ray is extremely small, a displacement amount Δx is approximately expressed by a mathematical expression (5).

$$\Delta x \approx L_2 \phi \qquad (5)$$

Here, the refraction angle φ is represented by a mathematical expression (6) using an X-ray wavelength λ and the phase shift distribution Φ(x) of the object H.

$$\varphi = \frac{\lambda}{2\pi} \frac{\partial \Phi(x)}{\partial x} \qquad (6)$$

Thus, the displacement amount Δx of the G1 image, caused by the X-ray refracted by the object H, relates to the phase shift distribution Φ(x) of the object H. A mathematical expression (7) represents a relation between the displacement amount Δx and a phase shift value ψ of the intensity modulated signal obtained from each pixel 40 of the FPD 20. The phase shift value ψ is a value of the phase shift between the case where the object H is present and the case where the object H is absent.

$$\psi = \frac{2\pi}{p_2} \Delta x = \frac{2\pi}{p_2} L_2 \varphi \qquad (7)$$

Accordingly, obtaining the phase shift value ψ of the intensity modulated signal of each pixel 40 provides the refraction angle φ using the mathematical expression (7). Using the mathematical expression (6), a derivative of the phase shift distribution Φ(x) is obtained. The derivative is integrated with respect to x. Thereby, the phase shift distribution Φ(x) of the object H, that is, the phase contrast image of the object H is produced. In this embodiment, the above-described phase shift value ψ is calculated using a fringe-scanning method described below.

In the fringe-scanning method, imaging is performed while one of the first and second absorption gratings 21 and 22 is translationally moved relative to the other in the x direction. In other words, the imaging is performed while the phases of the grating periods of the first and second absorption gratings 21 and 22 are changed. In this embodiment, the scan mechanism 23 moves the second absorption grating 22. The moiré fringes move in accordance with the movement of the second absorption grating 22. When the translational length (an amount of movement in the x direction) of the second absorption grating 22 reaches one period of the grating period (the grating pitch $p_2$) of the second absorption grating 22 (namely, when the phase change reaches 2π), the moiré fringes return to the original position. An image of the fringe image is captured with the FPD 20 every time the second absorption grating 22 is moved by the pitch which is an integral fraction of the grating pitch $p_2$. From each pixel, the intensity modulated signal is obtained from the captured fringe images. The phase differential image generator 32 in the image processor 14 calculates the phase shift value ψ of the intensity modulated signal for each pixel. The two-dimensional distribution of the phase shift value ψ corresponds to the phase differential image.

Figure 4:
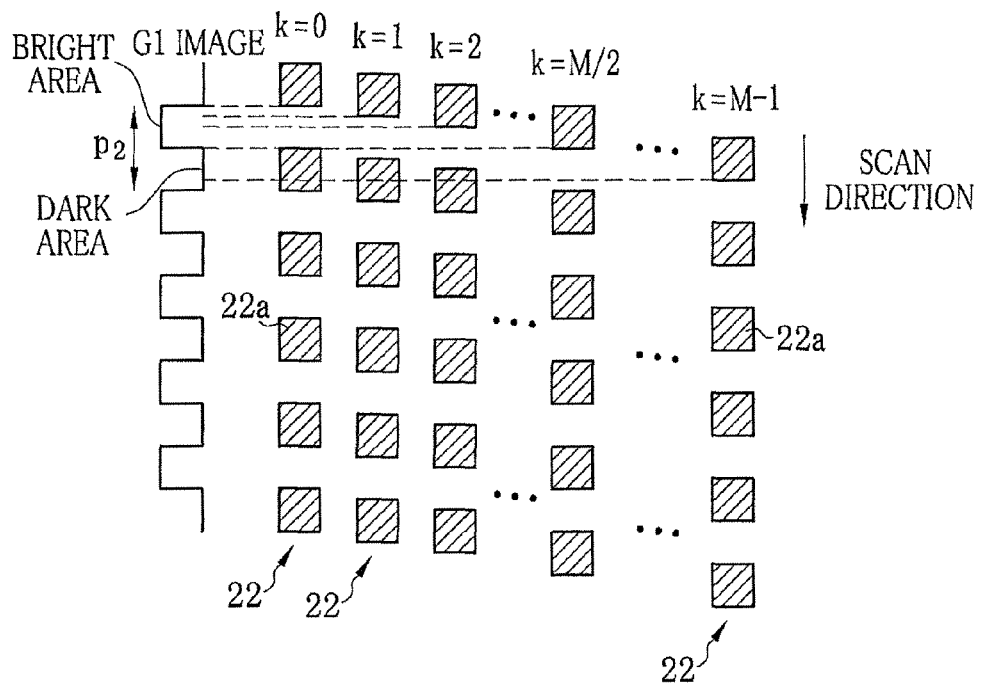
FIG. 4 is an explanatory view of a fringe-scanning method.

In FIG. 4, the second absorption grating 22 is moved with a scanning pitch ($p_2/M$), that is, the grating pitch $p_2$ divided by M (an integer equal to or larger than two). The scan mechanism 23 translationally moves the second absorption grating 22 at each of the M scanning positions where k=0, 1, 2, ..., M−1 in this order. In FIG. 4, an initial position of the second absorption grating 22 is a position (k=0) where the dark areas of the G1 image substantially coincide with the X-ray shield members 22a at the second absorption grating 22 in a state that the object H is absent. The initial position may be any position where k=0, 1, 2, ..., or M−1.

When the second absorption grating 22 is at the position where k=0, the X-ray passing though the second absorption grating 22 is mainly the X-ray not refracted by the object H. As the second absorption grating 22 is sequentially moved to positions where k=1, 2, ..., an X-ray component not refracted by the object H decreases while an X-ray component refracted by the object H increases in the X-ray passing through the second absorption grating 22. Particularly, when the second absorption grating 22 is at the position where k=M/2, the X-ray passing through the second absorption grating 22 is mainly the X-ray refracted by the object H. When the second absorption grating 22 moves past the position where k=M/2, on the contrary, the X-ray component refracted by the object H decreases while the X-ray component not refracted by the object H increases in the X-ray passing through the second absorption grating 22.

When an image is captured using the FPD 20 at each of the positions where k=0, 1, 2, ..., and M−1, M frames of pixel data are obtained from each pixel 40. Hereafter, a method to calculate the phase shift value ψ of the intensity modulated signal of each pixel 40 using the M frames of pixel data is described. A mathematical expression (8) represents pixel data $I_k(x)$ of each pixel when the second absorption grating 22 is located at a position k.

$$I_k(x) = A_0 + \sum_{n>0} A_n \exp\left[2\pi i \frac{n}{p_2}\left\{L_2 \varphi(x) + \frac{kp_2}{M}\right\}\right] \tag{8}$$

Here, "x" denotes a coordinate of the pixel in the x-direction. "$A_0$" denotes the intensity of the incident X-ray. "$A_n$" denotes a value corresponding to the contrast of the intensity modulated signal. (Here, "n" is a positive integer). "φ (x)" denotes the refraction angle φ in the form of a function of the coordinate x of the pixel 40.

Using a relational expression (9), the refraction angle φ(x) is represented by a mathematical expression (10).

$$\sum_{k=0}^{M-1} \exp\left(-2\pi i \frac{k}{M}\right) = 0 \tag{9}$$

$$\varphi(x) = \frac{p_2}{2\pi L_2} \arg\left[\sum_{k=0}^{M-1} I_k(x) \exp\left(-2\pi i \frac{k}{M}\right)\right] \tag{10}$$

Here, "arg [ ]" denotes calculation of argument and corresponds to the phase shift value ψ of the intensity modulated signal obtained from each pixel. Based on the mathematical expression (10), the phase shift value ψ is calculated using the M frames of pixel data (the intensity modulated signal) obtained from each pixel 40. Thereby, the refraction angle φ(x) is obtained. Thus, the derivative of the phase shift distribution Φ(x) is obtained.

Figure 5:
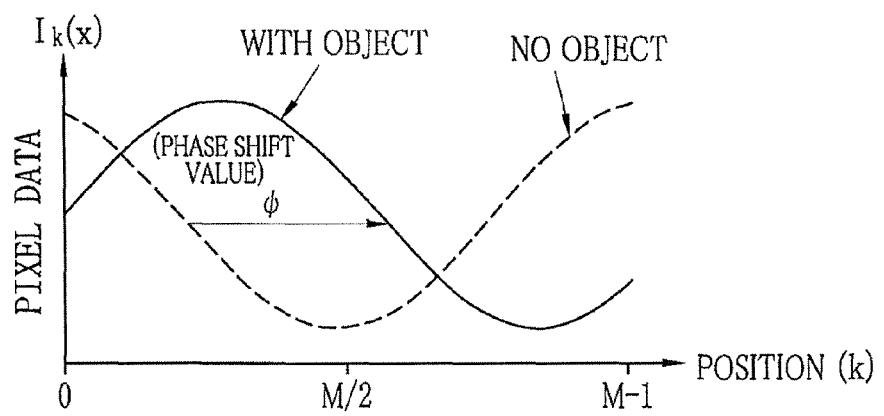
FIG. 5 is a graph showing pixel data (intensity modulated signal) changing in accordance with the fringe-scanning.

To be more specific, as shown in FIG. 5, the values of the M frames of pixel data obtained from the pixel 40 periodically change relative to the position k of the second absorption grating 22 in a period of the grating pitch $p_2$. In FIG. 5, broken lines denote changes in the pixel data (intensity modulated signal) when the object H does not exist. A solid line denotes changes in the pixel data (intensity modulated signal) when the object H exists. A phase difference between a waveform shown in the broken lines and a waveform shown in the solid line represents the phase shift value ψ of the intensity modulated signals obtained from each pixel.

In the above description, a y-coordinate in the y direction of the pixel 40 is not considered. To obtain the two dimensional distribution of the phase shift value ψ(x, y) in x and y directions, the same or similar operation is performed to each y-coordinate. The distribution of the phase shift value ψ(x, y) corresponds to the phase differential image. The refraction angle φ and the phase shift value ψ are in proportionality as shown in the mathematical expression (6), and are physical quantities corresponding to the derivative of the phase shift distribution Φ(x).

Figure 6:
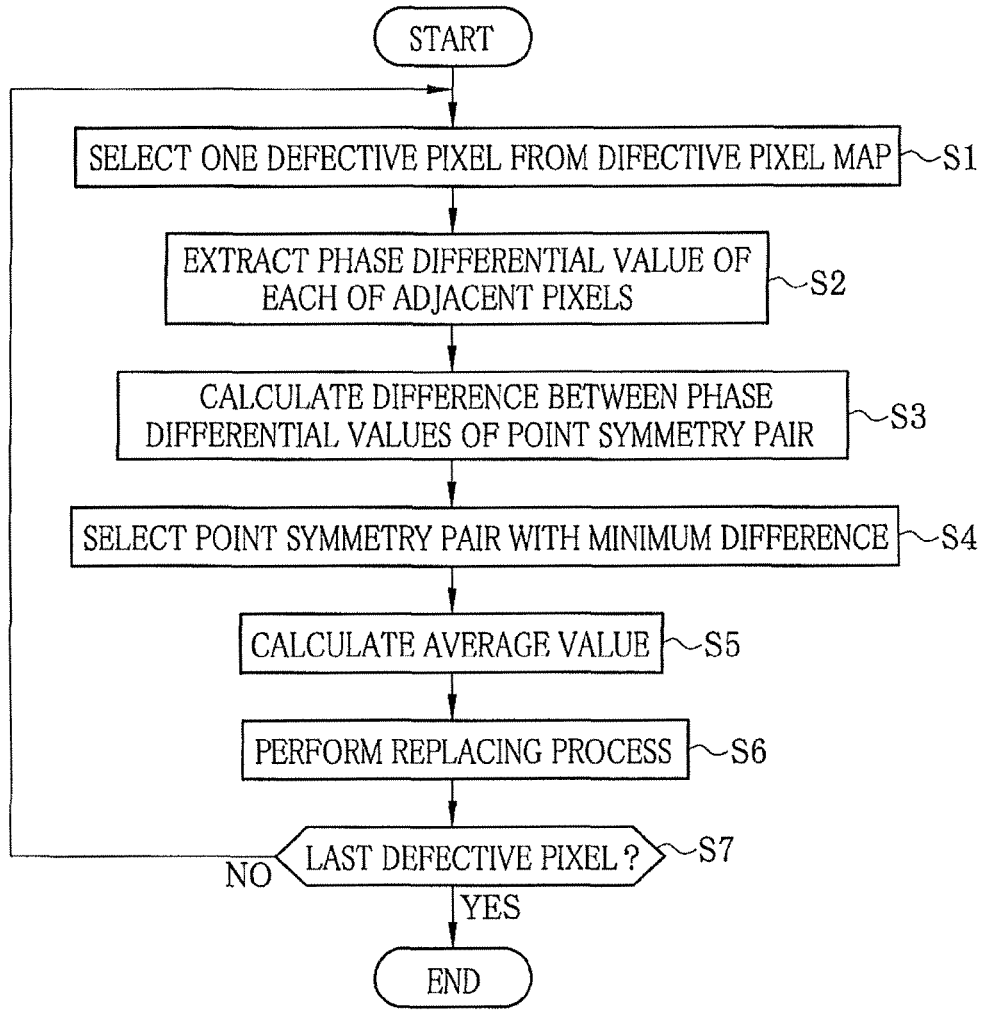
FIG. 6 is a flowchart showing steps for correcting a defective pixel.

Next, steps for correcting the defective pixel performed by the correction processing section 33 are described. As shown in a flowchart in FIG. 6, the correction processing section 33 performs the correction process of the phase differential image (distribution of the phase shift value ψ(x, y)) calculated by the phase differential image generator 32 based on the above-described principle. First, the correction processing section 33 selects a defective pixel from the defective pixel map stored in the defective pixel map storage 31 (step, hereafter abbreviated as "S", 1). Then, from the phase differential image inputted from the phase differential image generator 32, the correction processing section 33 extracts the phase differential values (the phase shift values ψ) of 8 pixels, adjacent to the defective pixel selected in the S1, respectively (S2).

Figure 7:
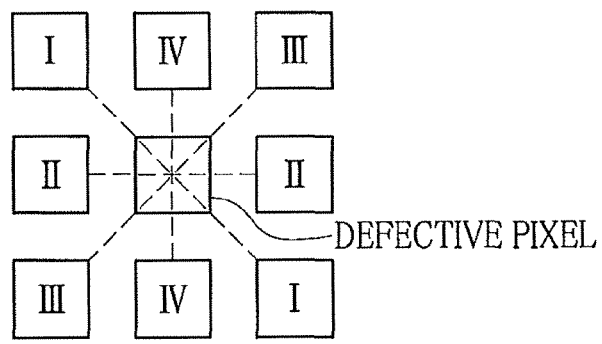
FIG. 7 is an explanatory view of point symmetric pairs.

As shown in FIG. 7, the 8 pixels adjacent to the defective pixel are formed into four point symmetry pairs I, II, III, and IV each of which is composed of 2 pixels symmetric with respect to the defective pixel. The correction processing section 33 calculates the difference between the phase differential values of 2 pixels in each of the four point symmetry pairs I, II, III, and IV (S3). If two or more defective pixels are adjacent to each other, the symmetry pair includes the defective pixel. In this case, the point symmetry pair including the defective pixel is excluded from the calculation for the difference in the phase differential values.

The correction processing section 33 identifies the point symmetry pair with the smallest absolute value of the difference between the phase differential values (S4). Then, the correction processing section 33 calculates the average value of the phase differential values of the selected point symmetry pair (S5). The correction processing section 33 performs a replacing process, that is, the correction processing section 33 replaces the phase differential value of the defective pixel with the calculated average value as the correction value (S6).

Thereafter, it is judged whether the defective pixel being selected is the last defective pixel (S7). When the defective pixel being selected is not the last one ("NO" in S7), the correction processing section 33 returns to the S1 again to select another defective pixel in the defective pixel map, and then repeats the S2 to the S6. Thus, the correction processing section 33 performs the steps for correcting the defective pixel to every defective pixel in the defective pixel map.

Thereafter, the corrected phase differential image is input to the phase contrast image generator 34. The phase contrast image generator 34 integrates the inputted phase differential image in the x axis to generate the phase shift distribution $\Phi(x, y)$ of the object H. The phase shift distribution $\Phi(x, y)$ is stored in the image storage 15 as the phase contrast image.

Figure 8:
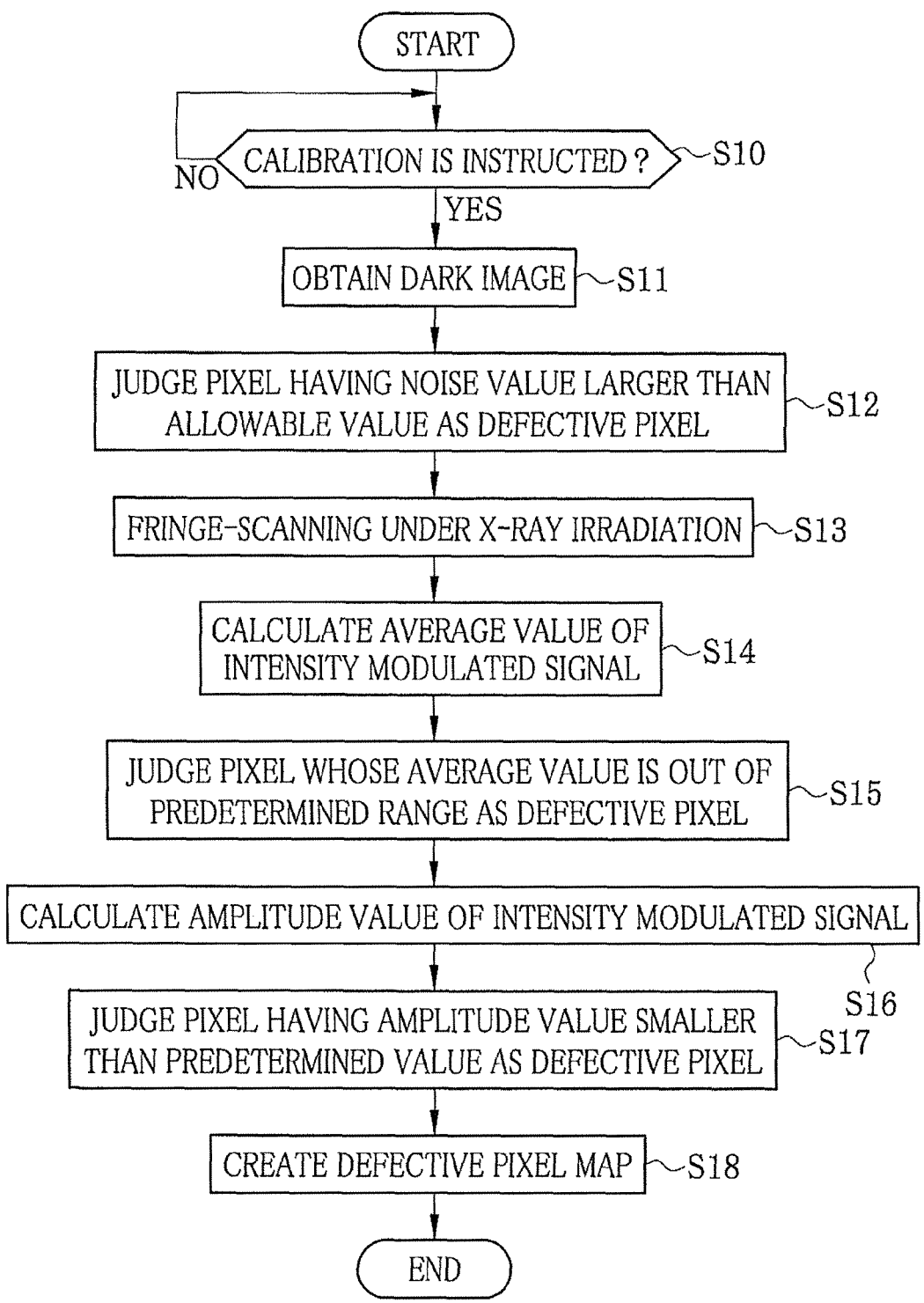
FIG. 8 is a flowchart showing steps for detecting defective pixels.

The steps for detecting the defective pixel performed by the defective pixel detector 30 during the calibration is described referring to the flowchart shown in FIG. 8. To perform the calibration, the system controller 18 follows an instruction from the operator inputted through the console 17 to control each section.

When the system controller 18 receives the instruction to perform the calibration (YES in S10), the system controller 18 allows the FPD 20 to perform imaging while prohibiting the X-ray irradiation of the X-ray source 11. The image data (hereafter, the image data obtained in the absence of X-ray irradiation is referred to as "dark image") obtained by the FPD 20 is stored in the memory 13 (S11).

The defective pixel detector 30 reads the dark image stored in the memory 13. The defective pixel detector 30 judges the pixel having the dark image (image data), that is, noise value of the pixel, larger than an allowable value (S12) as the defective pixel. Thereby, a pixel having large dark current (large leak current) due to the defect in the TFT switch or the like is judged as the defective pixel.

The system controller 18 allows the FPD 20 to perform the imaging operation, in a state that the object H is not arranged between the X-ray source 11 and the FPD 20 and that the X-ray is emitted from the X-ray source 11 at the predetermined intensity, while the scan mechanism 23 moves the second absorption grating 22 to each of the scanning positions k=0, 1, 2, . . . , and M−1. Hereafter, this imaging operation is referred to as "fringe-scanning imaging". The image data obtained at each of the scanning positions is stored in the memory 13 (S13).

Figure 9:
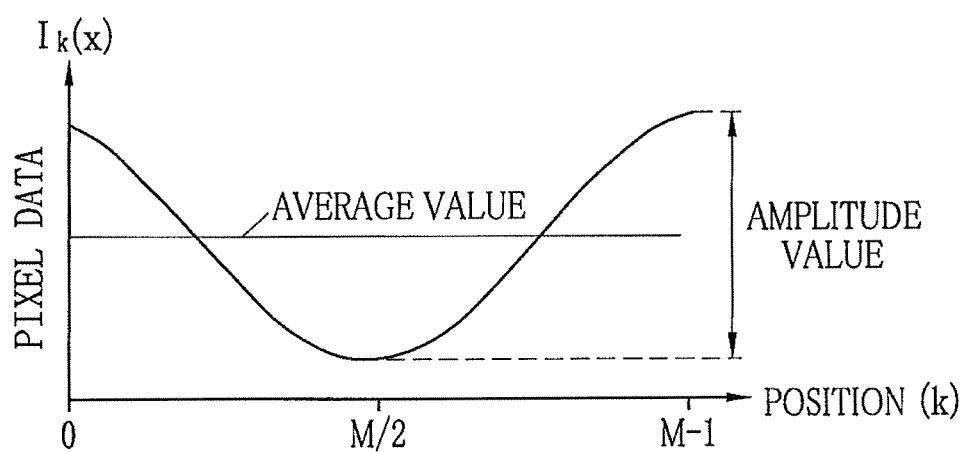
FIG. 9 is a graph showing an average value and an amplitude value of the intensity modulated signal.

The defective pixel detector 30 reads the multiple frames of image data stored in the memory 13. The defective pixel detector 30 calculates the average value of the pixel data (the intensity modulated signal) on a pixel-by-pixel basis (S14). To be more specific, as shown in FIG. 9, the multiple frames of pixel data $I_k(x)$ obtained at the scanning positions k are averaged to obtain the average value. If the number of the scanning positions k is too small to calculate the average value of the pixel data $I_k(x)$ from simple average, a sine wave most fitted to the pixel data $I_k(x)$ is obtained. The average value of the sine wave is used as the average value of the pixel data (the intensity modulated signal).

The defective pixel detector 30 judges the pixel as the defective pixel when the pixel has the average value, calculated in the S14, beyond the predetermined range (S15). The average value is proportional to the X-ray transmittance of the first and second absorption gratings 21 and 22 represented by a product of the X-ray transmittance of the first absorption grating 21 and the X-ray transmittance of the second absorption grating 22. In other words, the thicknesses (lengths in the z direction) and the widths (lengths in the x direction) of the first and second absorption gratings 21 and 22 affect the average value. In the S15, the defective pixels caused by the uneven thickness and the uneven width (irregular pitch) of the X-ray shield members 21a and 22a are detected. For example, when the X-ray shield member 21a or 22a is deformed in a direction to reduce the thickness or the width thereof, the X-ray shield property decreases because an amount of the X-ray leak increases. As a result, the average value of the intensity modulated signal increases. When the average value excesses an upper limit of a predetermined range, the pixel is judged as the defective pixel. On the contrary, when the X-ray shield member 21a or 22a is deformed in a direction to increase the thickness or the width thereof, the X-ray shield property increases. As a result, the average value of the intensity modulated signal decreases. When the average value falls short of a lower limit of a predetermined range, the pixel is judged as the defective pixel.

The defective pixel detector 30 calculates the amplitude value of the pixel data (the intensity modulated signal) for each pixel (S16). To be more specific, the amplitude value is a difference between the maximum value and the minimum value of the pixel data $I_k(x)$ obtained at every scanning position k. If the number of the scanning positions k is too small to obtain the amplitude value from the maximum and minimum values, a sine wave most fitted to the pixel data $I_k(x)$ is obtained. The amplitude value of the sine wave is used as the amplitude value of the pixel data (the intensity modulated signal).

The defective pixel detector 30 judges the pixel as the defective pixel when the pixel has the amplitude value, calculated in S16, smaller than a predetermined value (S17). The amplitude value represents a difference between the signal value obtained when the phase difference between the grating periods of the first and second absorption gratings 21 and 22 is "0" and the signal value obtained when the phase difference between the grating periods of the first and second absorption gratings 21 and 22 is "π", that is, the contrast. When there is irregularity in the grating pitch or in the opening width in one of the first and second absorption gratings 21 and 22, the amplitude value of the intensity modulated signal of the pixel corresponding to the irregular part of the grating decreases. The pixel is judged as the defective pixel when the amplitude value falls short of the predetermined value.

The defective pixel detector 30 integrates the defective pixel information obtained in the S15 and S17 to create the defective pixel map representing the positional information of the defective pixel. The defective pixel detector 30 inputs the defective pixel map in the defective pixel map storage 31 (S18). At that time, if the defective pixel map already exists in the defective pixel map storage 31, the existing defective pixel map is updated (replaced with the inputted defective pixel map).

Next, an operation of the above-configured X-ray imaging system 10 is described. When the operator inputs an instruction of the calibration through the console 17, each section of the X-ray imaging system 10 works in cooperation to perform the above-described calibration operation. The defective pixel detector 30 performs the detection process of the defective pixel. The defective pixel map created based on the detected defective pixels is stored in the defective pixel map storage 31.

Thereafter, when the operator inputs an instruction for imaging using the console 17, with the object H being arranged between the X-ray source 11 and the FPD 20, each section of the X-ray imaging system 10 works in cooperation to execute the above-described imaging operation. Thus, the phase differential image, that is, the distribution of the phase shift value $\psi(x, y)$ is produced. The defective pixel is corrected based on the defective pixel map. Thereafter, the phase contrast image is produced and displayed on the monitor.

Figure 10A:
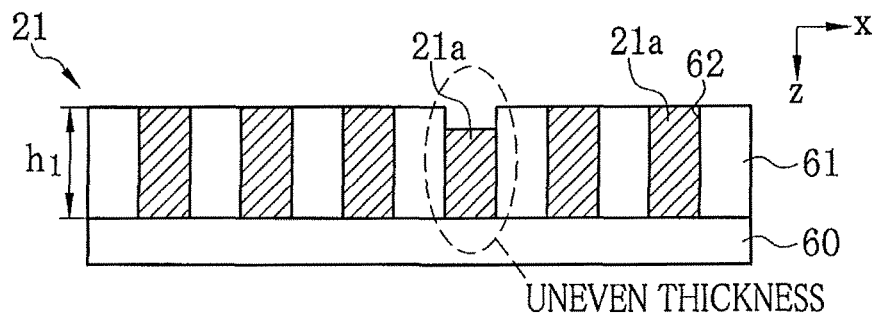
FIGS. 10A, 10B, and 10C are cross-sectional views of the first absorption grating showing types of deformation of the first grating causing a defective pixel.
Figure 10B:
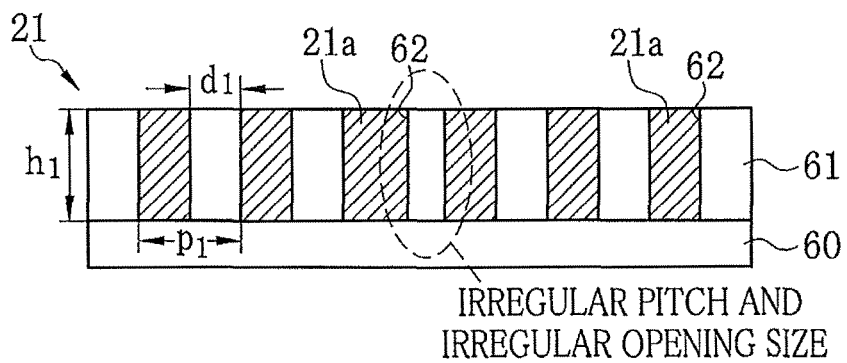
Figure 10C:
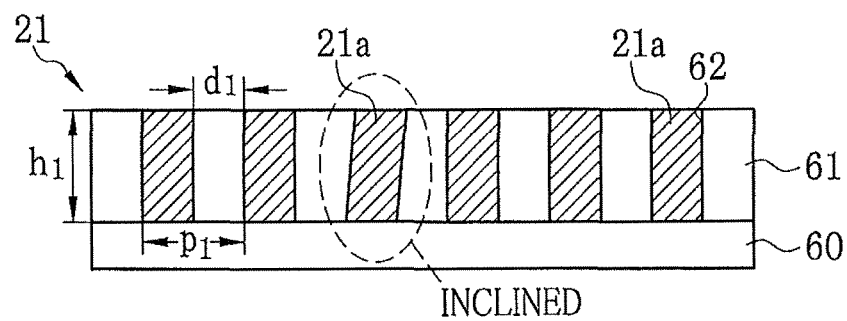

Next, the types of the defective pixels caused by the grating deformation are described. The defective pixels are detected through the above-described detection process. FIGS. 10A to 10C illustrate types of the deformation occurring in the first absorption grating 21. Here, the X-ray shield member 21a has an X-ray transmission substrate 60 composed of glass and the like and a layer 61 such as a resist film layered on the X-ray transmission substrate 60. The layer 61 is formed with grooves 62 filled with High X-ray absorption material such as gold (Au).

FIG. 10A shows local deformation of the X-ray shield member 21a where the thickness is uneven. In an area surrounded by a broken line, the thickness of the X-ray shield member 21a is smaller than the design thickness $h_1$ due to insufficient filling of the high X-ray absorption material, for example. The X-ray transmittance of this area increases and thereby the average value of the intensity modulated signals from the pixel corresponding to this area increases. As a result, the pixel corresponding to this area is judged as the defective pixel in the S15. The increase in the X-ray transmittance also affects the amplitude value of the intensity modulated signal, so the corresponding pixel may be judged as the defective pixel in the S17.

FIG. 10B shows local deformation of the X-ray shield member 21a where the width is uneven (irregular pitch). In an area surrounded by a broken line, the width of the X-ray shield member 21a is larger than the other X-ray shield members 21a due to the production error of the groove 62, for example. Accordingly, the pitch and the opening width are different from the design pitch $p_1$ and the design width $d_1$, respectively. A mismatch between this area of the first absorption grating 21 and the second absorption grating 22 lowers the amplitude value of the intensity modulated signal. As a result, the pixel corresponding to this area is judged as the defective pixel in the S17. Irregularities in the pitch and the opening width also affect the average value of the intensity modulated signal, so the corresponding pixel may be judged as the defective in the S15.

FIG. 10C shows local deformation where one of the X-ray shield members 21a is inclined or tilted. The inclination of the X-ray shield member 21a often occurs when the layer 61 is made from a relatively soft resist material. An area surrounded by the broken line causes vignetting of the X-ray due to the inclination of the X-ray shield member 21a. The inclination of the X-ray shield member 21a results in changes in the pitch and the opening width. Accordingly, the pixel corresponding to the area surrounded by the broken line is judged as the defective pixel in the S17 as with the example shown in FIG. 10B. The inclination of the X-ray shield member 21a also affects the average value of the intensity modulated signals, so the corresponding pixel may be judged as the defective pixel in the S15.

In the above examples, the deformation appears in only one of the X-ray shield members 21a. In the actual conditions, however, the deformation often appears in two or more X-ray shield members 21a. In this case, the average value and the amplitude value of the intensity modulated signal vary more significantly. The same holds true for the deformation in the second absorption grating 22.

Figure 11:
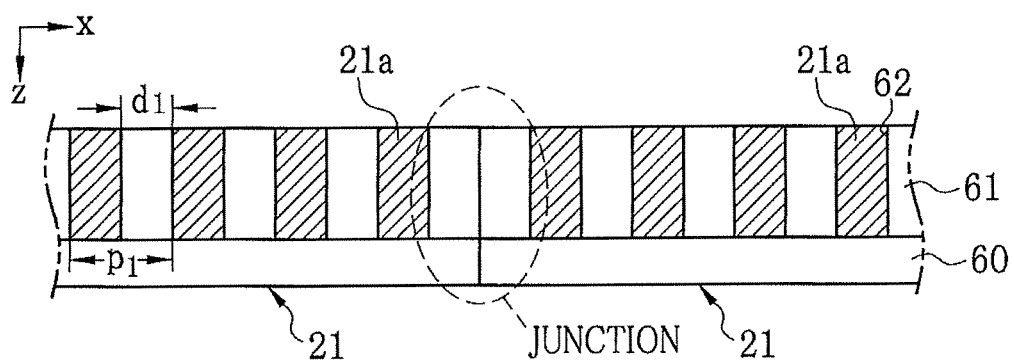
FIG. 11 is a cross-sectional view of the first absorption grating in which two or more gratings are joined.

To widen field of view of the X-ray imaging system 10 of this embodiment, it is necessary to upsize the first and second absorption gratings 21 and 22. As shown in FIG. 11, to obtain an upsized first absorption grating 24, the two or more first absorption gratings 21 are joined to each other. To obtain an upsized second absorption grating 25, the two or more second absorption gratings 22 are joined to each other.

As shown in FIG. 11, in the upsized first absorption grating 24, the width between the X-ray shield members 21a at a junction surrounded by a broken line is larger than the other widths. Accordingly, the pitch and the opening width in the area surrounded by the broken line are different from the design pitch $p_1$ and the design width $d_1$, respectively. The same holds true for the upsized second absorption grating 25.

In the detection process of the defective pixel, the pixel corresponding to the junction is detected as the defective pixel, and then the correction process is performed. The detection process of the defective pixel according to the present invention is also suitable for an X-ray imaging system having a large grating composed of two or more gratings joined together as described above.

In the above embodiments, the defective pixel is detected using the amplitude value and the average value as the characteristic values of the intensity modulated signals. Instead of using the amplitude value, one of a maximum value, a minimum value, a variance, a standard deviation, and visibility may be used. These values change in accordance with the contrast of the intensity modulated signal. Here, the visibility is a value represented by $(I_{max}-I_{min})/(I_{max}+I_{min})$ where $I_{max}$ denotes the maximum value of the intensity modulated signal and $I_{min}$ denotes the minimum value of the intensity modulated signal.

A period of the intensity modulated signal may be used as the characteristic value of the intensity modulated signal in detecting the defective pixel. The period of the intensity modulated signal changes in accordance with the changes in the grating pitches $p_1$ and $p_2$ of the first and second absorption gratings 21 and 22.

In the above embodiments, when the distance between the X-ray source 11 and the FPD 20 is increased, blur of the G1 image due to the size of the x-ray focal point 11a (generally in a range approximately from 0.1 mm to 1 mm) may degrade the image quality of the phase contrast image. To prevent the degradation in the image quality of the phase contrast image, a multi-slit (radiation-source grating) may be arranged in the immediate vicinity of the x-ray focal point 11a.

The multi-slit is an absorption grating having the same or similar configuration as the first and second absorption gratings 21 and 22. The multi-slit has multiple X-ray shield members extended in one direction (in this embodiment, the y direction) and periodically arranged in the same direction as the X-ray shield members 21a and 22a of the first and second absorption gratings 21 and 22 (in this embodiment, the x direction). To prevent blur of the G1 image, the multi-slit partly shields the X-ray emitted from the X-ray source 11 to reduce the size of the effective focal point in the x direction and forms a plurality of point sources (dispersion light source) in the x direction.

In the above embodiments, the first and second absorption gratings 21 and 22 are configured to linearly project the X-ray passed through their slits. The present invention is not limited to the above. The first and second absorption gratings 21 and 22 may be configured to diffract the X-ray at their slits to generate the so-called Talbot effect (see, for example, the configuration disclosed in U.S. Pat. No. 7,180,979 corresponding to WO 2004/058070). In this case, the distance $L_2$ between the first and second absorption gratings 21 and 22 needs to be set at the Talbot length, and a phase grating (phase diffraction grating) can be used instead of the first absorption grating 21. The phase grating, used instead of the first absorption grating 21, forms the fringe image (self image) generated by the Talbot effect at the second absorption grating 22.

The only difference between the phase grating and the absorption grating is the thickness of the high X-ray absorption material (the X-ray shield member). The thickness of the X-ray shield member of the absorption grating is at least approximately 30 μm (Au equivalent thickness). On the other hand, the thickness of the X-ray shield member of the phase grating is approximately in a range from 1 μm to 5 μm. In the phase grating, the high X-ray absorption material modulates the phase of the incident X-ray emitted from the X-ray source 11 by a predetermined value (preferably, π or π/2). Thereby, a fringe image (the self image) is generated due to the Talbot effect. When the thickness and the pitch of the high X-ray absorption material are locally or partially irregular in the phase grating, the fringe image corresponding to the irregular portion or area of the phase grating deteriorates. In this case, it is necessary to detect the pixel corresponding to the deteriorated fringe image as the defective pixel. The detection process of the defective pixel of the present invention can also detect the defective pixel when a phase grating is used instead of the first absorption grating 21.

In this embodiment, the object H is arranged between the X-ray source 11 and the first absorption grating 21. The phase contrast image can be produced even if the object H is arranged between the first absorption grating 21 and the second absorption grating 22.

(Second Embodiment)

Figure 12:
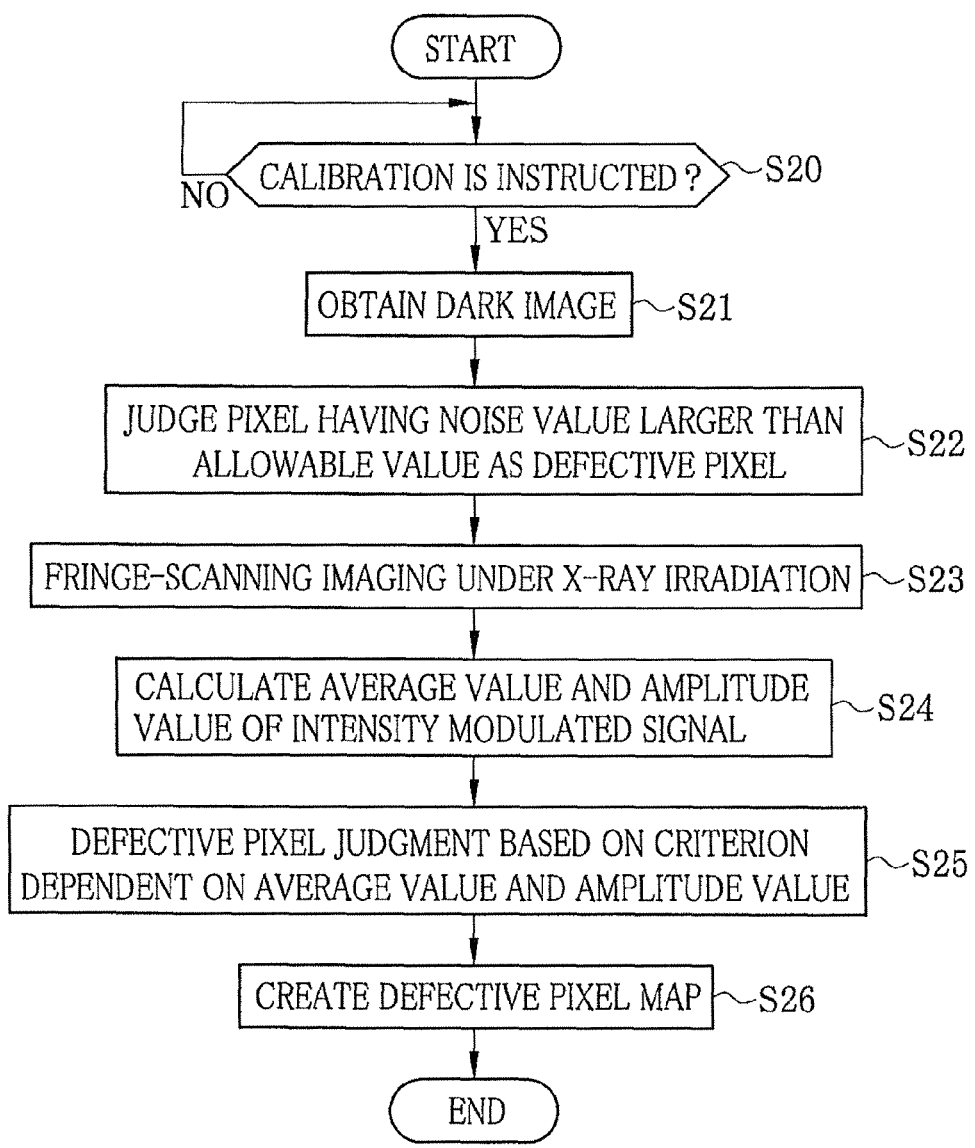
FIG. 12 is a flowchart showing steps of detecting a defective pixel according to a second embodiment of the present invention.

Next, a second embodiment of the present invention is described. The second embodiment is a variant of the detection process of the defective pixel performed by the defective pixel detector 30. In this embodiment, the correction processing section 33 performs the detection process following a flowchart shown in FIG. 12.

First, as with the first embodiment, when the calibration is instructed ("YES" in S20), the FPD 20 obtains the image data (the dark image) in a state that the X-ray irradiation from the X-ray source 11 or X-ray exposure is prohibited. The obtained dark image is stored in the memory 13 (S21). The defective pixel detector 30 reads the dark image stored in the memory 13. The defective pixel detector 30 judges a pixel having the pixel data (pixel noise value) larger than an allowable value as the defective pixel (S22).

Next, the fringe-scanning imaging is performed in a state that the X-ray having predetermined intensity is emitted from the X-ray source 11 and that the object H is not arranged between the X-ray source 11 and the FPD 20. The image data obtained at each scanning position is stored in the memory 13 (S23). The defective pixel detector 30 reads the multiple frames of image data stored in the memory 13. The defective pixel detector 30 calculates the average value and the amplitude value of the pixel data (the intensity modulated signal) on the pixel-by-pixel basis, following the same or similar steps described in the first embodiment (S24).

Figure 13:
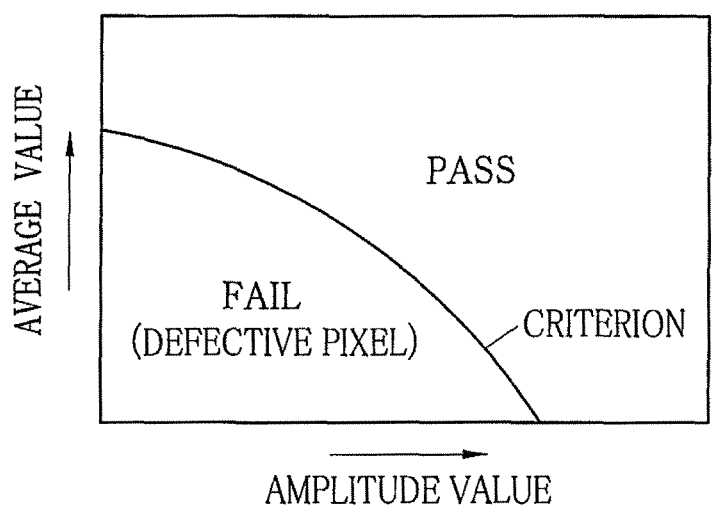
FIG. 13 is a graph showing a criterion dependent on the average value and the amplitude value of the intensity modulated signal.

Using a criterion dependent on the average value and the amplitude value of the intensity modulated signal as shown in FIG. 13, the defective pixel detector 30 judges whether a pixel is defective or not on the pixel-by-pixel basis (S25). The criterion shown in FIG. 13 is approximately inversely proportional to both the average value and the amplitude value. The defective pixel detector 30 judges a pixel having the average value and the amplitude value lower than the criterion as the defective pixel. The criterion is set or stored in the defective pixel detector 30 in advance in a form of a function or a matrix chart, for example.

Thereafter, the defective pixel detector 30 integrates defective pixel information obtained in the S22 and the defective pixel information obtained in S25 to create the defective pixel map representing the positional information of the defective pixel(s). The defective pixel detector 30 inputs the created defective pixel map in the defective pixel map storage 31 (S26).

In this embodiment, as described above, the defective pixel is detected using the criterion dependent on the average value and the amplitude value. Accordingly, "a pixel having a small average value and a large amplitude value" and "a pixel having a small amplitude value and a large average value" are not judged as the defective pixels. Because there is a possibility that the above-described phase shift can be identified when a pixel has one of the large average value and the large amplitude value, such pixel is not judged as the defective pixel and contributes to the production of the phase contrast image.

It is preferable that the defective pixel detector 30 stores multiple criteria and the operator can select one or more criteria as necessary through the operation of the console 17. When the X-ray imaging system 10 is used for performing medical diagnoses, for example, it is preferable to change the criteria in accordance with imaging conditions (e.g. a body site to be imaged) selected using the console 17. Each of the criteria may be determined in advance in view of clinical research or the like.

The defective pixel information obtained in the S22 is information on the defective pixel caused by the defect of the FPD 20. The defective pixel information obtained in the S25 is information on the defective pixel caused by the defect of the first and second absorption gratings 21 and 22. Accordingly, it is preferable to store the defective pixel information in the defective pixel map storage 31 separately in a distinguishable manner based on the cause of the defect. For example, the defective pixel information may be stored in different storage sectors in the defective pixel map storage 31 depending on the causes of the defect. At the time of maintenance, the defect pixel information is read from the defective pixel map storage 31, and thereby the cause of the defect is easily identified. Thus, the maintainability enhances.

In this embodiment, the information on the defective pixel caused by the FPD 20 is detected using the dark image. In addition, it is preferable to obtain the defective pixel information from a uniform X-ray absorption image produced with uniform X-ray irradiation on the FPD 20 in a state that the first and second absorption gratings 21 and 22 are removed or retracted.

(Third Embodiment)

In the above embodiments, the second absorption grating 22 is provided independently of the FPD 20. With the use of an X-ray detector disclosed in U.S. Pat. No. 7,746,981 corresponding to Japanese Patent Laid-Open Publication No. 2009-133823, the second absorption grating 22 can be eliminated. The X-ray image detector is a direct conversion type X-ray image detector provided with a conversion layer and charge collection electrodes. The conversion layer converts the X-ray into electric charge. The charge collection electrodes collect the converted electric charge. The charge collection electrode in each pixel is composed of linear electrode groups arranged to have mutually different phases. Each linear electrode group is composed of linear electrodes arranged at a predetermined period and electrically connected to each other. The charge collection electrode constitutes the intensity modulator.

Figure 14:
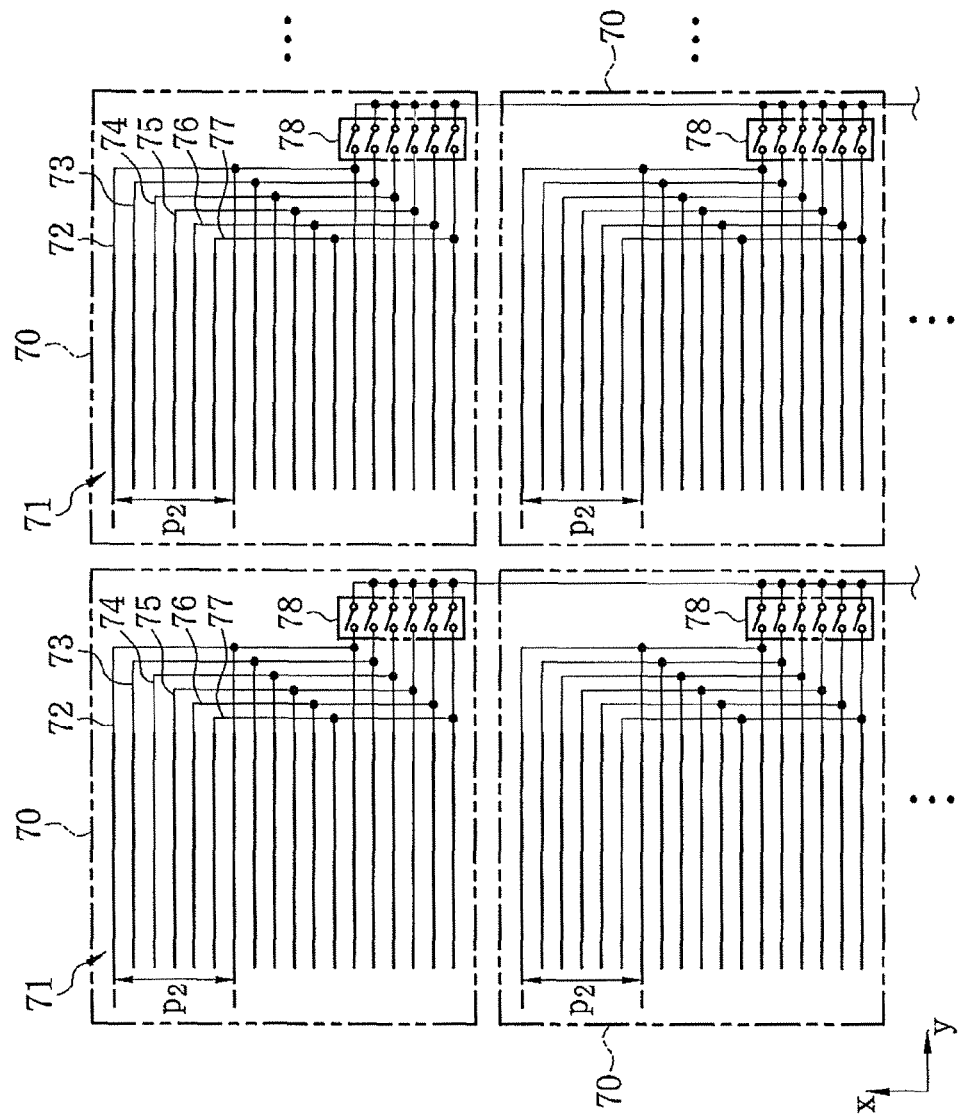
FIG. 14 is a diagram showing a configuration of an X-ray image detector used in a fourth embodiment of the present invention.

In FIG. 14, the X-ray image detector (FPD) of this embodiment is composed of pixels 70 arranged in two dimensions (x and y directions) at a constant pitch. In each pixel 70, a charge collection electrode 71 is formed. The charge collection electrode 71 collects electric charge converted by the conversion layer. The charge collection electrode 71 is composed of first to sixth linear electrode groups 72 to 77. The phase of the arrangement period of each linear electrode group is shifted by π/3. For example, when the phase of the first the linear electrode group 72 is zero, the phase of the second linear electrode group 73 is π/3, the phase of the third linear electrode group 74 is 2π/3, the phase of the fourth linear electrode group 75 is π, the phase of the fifth linear electrode group 76 is 4π/3, and the phase of the sixth linear electrode group 77 is 5π/3. Thus, the electric charge generated in the pixel 70 is accumulated through the linear electrode groups 72 to 77.

Each pixel 70 is further provided with a switch group 78 for reading the electric charge collected by the charge collection electrode 71. The switch group 78 is composed of TFT switches respectively provided to the first to the sixth linear electrode groups 72 to 77. The switch group 78 is controlled to separately read the electric charge collected by each of the first to the sixth linear electrode groups 72 to 77. Thereby, six different fringe images with mutually different phases are obtained per image capture. The phase contrast image is produced based on the six different fringe images.

Using the above-configured X-ray image detector instead of the FPD 20 eliminates the need for the second absorption grating 22 in the imaging unit 12. As a result, cost is reduced and the lower-profile is achieved. In this embodiment, fringe images whose intensities are modulated at different phases are obtained per image capture. Accordingly, physical scanning for the fringe-scanning is unnecessary and thus the scan mechanism 23 is eliminated. Instead of the charge collection electrode 71, other charge collection electrodes disclosed in the U.S. Pat. No. 7,746,981 may be used.

In another embodiment not using the second absorption grating 22, the fringe image (G1 image) obtained by the X-ray image detector may be periodically sampled while the phase is changed through signal processing. Thereby, the intensity of the fringe image is modulated.

In the above embodiments, the X-ray source 11 for emitting the cone beam X-ray is used as an example. An X-ray source for emitting collimated or parallel X-ray may be used. In this case, mathematical expressions (11) to (13) are used instead of the above mathematical expressions (1) to (3), respectively.

$$p_2 = p_1 \quad (11)$$

$$Z = m\frac{p_1^2}{\lambda} \quad (12)$$

$$L_2 < \frac{p_1^2}{\lambda} \quad (13)$$

In addition to the radiation imaging system used for performing medical diagnoses, the above-described embodiments can be applied to other radiation imaging systems, for example, an industrial radiation imaging system such as non-destructive inspection. Instead of or in addition to the X-ray, gamma rays and the like may be used as the radiation.

Various changes and modifications are possible in the present invention and may be understood to be within the present invention.

What is claimed is:

1. A defective pixel detection apparatus used in an X-ray radiation imaging system, the X-ray radiation imaging system including a grating, an intensity modulator, and an X-ray radiation image detector, the grating passing X-ray radiation emitted from an X-ray radiation source to form a first fringe image, the intensity modulator modulating intensity of the first fringe image at each of relative positions to form two or more second fringe images, the relative positions differing in phase with respect to a period pattern of the first fringe image, the X-ray radiation image detector detecting the second fringe image, the defective pixel detection apparatus comprising:

a characteristic value obtaining section for obtaining a characteristic value from an intensity modulated signal on a pixel-by-pixel basis, the intensity modulated signal representing a relation between a relative position and a pixel value; and a defective pixel detecting section for detecting a defective pixel based on the characteristic value.

2. The defective pixel detection apparatus of claim 1, wherein the characteristic value comprises at least one of an amplitude value, an average value, a maximum value, a minimum value, a variance, a standard deviation, visibility, and a period.

3. The defective pixel detection apparatus of claim 2, wherein the characteristic value comprises the average value and the amplitude value, and the defective pixel detecting section detects the defective pixel based on a criterion dependent on the characteristic value.

4. The defective pixel detection apparatus of claim 1, wherein the defective pixel detecting section further detects the defective pixel based on a dark image obtained by the X-ray radiation image detector in the absence of the X-ray radiation.

5. A defective pixel detection method used in an X-ray radiation imaging system, the X-ray radiation imaging system including a grating, an intensity modulator, and an X-ray radiation image detector, the grating passing X-ray radiation emitted from an X-ray radiation source to form a first fringe image, the intensity modulator modulating intensity of the first fringe image at each of relative positions to form two or more second fringe images, the relative positions differing in phase with respect to a period pattern of the first fringe image, the X-ray radiation image detector detecting the second fringe image, the defective pixel detection method comprising:

obtaining a characteristic value from an intensity modulated signal on a pixel-by-pixel basis, the intensity modulated signal representing a relation between a relative position and a pixel value; and detecting a defective pixel based on the characteristic value.

6. An X-ray radiation imaging system comprising:

a grating for passing X-ray radiation emitted from an X-ray radiation source to form a first fringe image;

an intensity modulator for modulating intensity of the first fringe image at each of relative positions to form two or more second fringe images, the relative positions differing in phase with respect to a period pattern of the first fringe image;

an X-ray radiation image detector for detecting the second fringe images;

a characteristic value obtaining section for obtaining a characteristic value from an intensity modulated signal on a pixel-by-pixel basis, the intensity modulated signal representing a relation between a relative position and a pixel value; and a defective pixel detecting section for detecting a defective pixel based on the characteristic value.

7. The X-ray radiation imaging system of claim 6, wherein the characteristic value comprises at least one of an amplitude value, an average value, a maximum value, a minimum value, a variance, a standard deviation, visibility, and a period.

8. The X-ray radiation imaging system of claim 7, wherein the characteristic value comprises the average value and the amplitude value, and the defective pixel detecting section detects the defective pixel based on a criterion dependent on the characteristic value.

9. The X-ray radiation imaging system of claim 6, further comprising storage for storing position information of the defective pixel detected by the defective pixel detecting section.

10. The X-ray radiation imaging system of claim 9, wherein the position information stored in the storage is updated when new position information of the defective pixel is generated by the defective pixel detecting section.

11. The X-ray radiation imaging system of claim 10, wherein the defective pixel detecting section further detects the defective pixel based on a dark image obtained by the X-ray radiation image detector in the absence of the X-ray radiation.

12. The X-ray radiation imaging system of claim 11, wherein the defective pixel detecting section stores the position information of the defective pixel detected based on the dark image separately from the position information of the defective pixel detected based on the characteristic value of the intensity modulated signals in a distinguishable manner in the storage.

13. The X-ray radiation imaging system of claim 6, wherein the intensity modulator is composed of a second grating including a periodic pattern in the same direction as the first fringe image, and a scanning section for moving at least one of the first grating and the second grating at a predetermined pitch.

14. The X-ray radiation imaging system of claim 13, wherein the first and second gratings comprise absorption gratings.

15. The X-ray radiation imaging system of claim 13, wherein the first grating comprises a phase grating.

16. The X-ray radiation imaging system of claim 6, wherein each of the pixels include a conversion layer for converting the X-ray radiation into electric charge and a charge collection electrode for collecting the electric charge, and wherein the charge collection electrode is composed of multiple linear electrode groups arranged to include mutually different phases, the linear electrode groups include periodic patterns in the same direction as the first fringe image, and wherein the intensity modulator is composed of the charge collection electrode.

* * * * *